United States Patent [19]

Untch et al.

[11] 4,151,297

[45] Apr. 24, 1979

[54] BICYCLO [3.1.0] HEXYL-SUBSTITUTED ETHYLAMINO CARBONYL PHENOXY CARDIOVASCULAR AGENTS

[75] Inventors: Karl G. Untch, Los Altos; Stefan H. Unger, Palo Alto; Brian Lewis, Mountain View, all of Calif.

[73] Assignee: Syntex (U.S.A.) Inc., Palo Alto, Calif.

[21] Appl. No.: 846,953

[22] Filed: Oct. 31, 1977

[51] Int. Cl.[2] ................ C07B 103/737; C07D 263/06; A61K 31/165; A61K 31/42

[52] U.S. Cl. ................................ 424/304; 260/501.17; 260/558 R; 260/559 A; 562/595; 424/324; 424/272

[58] Field of Search .......... 260/559 A, 558 R, 501.17; 562/595; 424/304, 316, 324

[56] References Cited

U.S. PATENT DOCUMENTS

| | | | |
|---|---|---|---|
| 4,00,193 | 12/1976 | Lunts et al. | 260/559 A X |
| 3,676,493 | 7/1972 | Smith | 260/559 A |
| 3,723,524 | 3/1973 | Augstein et al. | 260/559 A X |
| 4,000,192 | 12/1976 | Lunts et al. | 260/559 A X |
| 4,059,621 | 11/1977 | Vincent et al. | 260/559 A X |

FOREIGN PATENT DOCUMENTS

| | | | |
|---|---|---|---|
| 1245357 | 7/1967 | Fed. Rep. of Germany | 260/559 A |

*Primary Examiner*—Allen B. Curtis

*Attorney, Agent, or Firm*—Richard J. Hammond; Gerard A. Blaufarb

[57] ABSTRACT

1-Alkylamino-3-(3- or 4-[2-(endobicyclo[3.1.0]-hex-6-yl)ethylaminocarbonyl]-1-phenoxy)-2-propanol and substituted derivatives thereof and methods for preparing such compounds are disclosed. 5-(3- Or 4-[2-(endobicyclo[3.1.0]hex-6-yl)ethylaminocarbonyl]-phenoxy)methyl 3-alkyl-2-optionally substituted oxazolidine and derivatives thereof, and methods for preparing such compounds are also disclosed. These compounds exhibit cardiovascular acitivity and are useful in the treatment of abnormal heart condition as well as hypertension in mammals. The former compounds are prepared by treatment of the corresponding 1,2-epoxy-3-(3- or 4-[2-(endobicyclo[3.1.0]hex-6-yl)-ethylaminocarbonyl]-phenoxy)propane with the desired alkylamine or by base or acid hydrolysis of the corresponding 5-(3- or 4-[2-(endobicyclo[3.1.0]hex-6-yl)-ethylaminocarbonyl)-3-alkyl oxazolidine. The latter compounds are prepared from the corresponding 1-alkylamino-3-(3- or 4-[2-(endobicyclo[3.1.0]hex-6-yl)ethylaminocarbonyl]-1-phenoxy)-2-propanol by treatment with an aldehyde having the desired optional substituent or by treating a 3- or 4-(2-(endobicyclo[3.1.0]hex-6-yl)ethylaminocarbonyl)-optionally substituted phenol with a 5-tosyloxy or mesyloxymethyl 3-alkyl)-methyloxazolidine-2-optionally substituted oxazolidine.

57 Claims, No Drawings

BICYCLO [3.1.0] HEXYL-SUBSTITUTED ETHYLAMINO CARBONYL PHENOXY CARDIOVASCULAR AGENTS

FIELD OF THE INVENTION

This invention relates to 1-alkylamino-3-(3- or 4-[2-(endobicyclo[3.1.0]hex-6-yl)ethylaminocarbonyl]-phenoxy)-2-propanol and pharmaceutically acceptable salts thereof; to 1-alkylamino-3-(3- or 4-[2-(endobicyclo[3.1.0]hex-6-yl)-ethylaminocarbonyl]-substituted phenoxy)-2-propanol and pharmaceutically acceptable salts thereof and to methods for preparing such compounds. This invention further relates to 5-(3- or 4-[2-(endobicyclo[3.1.0]hex-6-yl)ethylaminocarbonyl]-phenoxymethyl)-3-alkyl-2-optionally substituted oxazolidone, to pharmaceutically acceptable salts thereof and to methods for the preparation of these compounds. This invention also relates to pharmaceutical compositions comprising one or more of the above compounds and to methods for treating cardiac disorders and hypertension in mammals.

At the present time, the compound most frequently used in the United States for treatment of cardiac arrhythmias and hypertension is 1-(isopropylamino)-3-(1-naphthoxy)-2-propanol (e.g. Propranol). Propranol is believed to achieve its therapeutic action by competing with beta-adrenergic receptor stimulating agents for available beta receptor sites. When access to such sites is blocked by propranol, the chronotropic, inotropic and vasodilator response to beta-adrenergic stimulation is decreased. Such activity is however not specific. Not only are heart muscle receptor sites affected, but lung and related organs are found to be influenced by this drug. Contraindication is therefore indicated for patients with bronchial asthma, allergic rhinitis, sinus brachycardia and the like.

In order to overcome the disadvantages present in the non-specific beta-adrenergic blocking agents, drugs specific for heart muscle blockage only have been developed. See for example U.S. Pat. No. 3,408,387. One of the most active compounds of the selective beta blockers is N-[4-[2-hydroxy-3-[(1-methylethyl)amino]-propoxy]acetanilide, e.g. practolol. Unfortunately, this compound exhibits disadvantageous side effects in man.

U.S. Pat. No. 3,897,441 discloses certain 3-(5-substituted aminocarbonylthiazol-2-yloxy)-2-propanol-1-amines and U.S. patent application Ser. No. 796,342 filed July 19, 1976 discloses various 5-carbocyclic alkylaminocarbonylthiazol-2-yloxy compounds. Both these compound-types display beta adrenergic blocking activity and cardiac selectivity. A novel analogous class of compounds having surprising blocking activity, cardiac selectivity and reduced cardiac depression has now been discovered. These compounds are especially felicitous for the treatment or palliation of angina pectoris and cardiac arrhythmias and because of their cardiac selectivity can be safely applied to patients suffering from asthma or chronic obstructive lung disease.

SUMMARY

In summary, the compounds of the present invention can be represented by the generic formula:

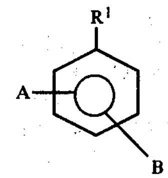

(I)

where $R^1$ is the radical

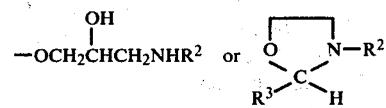

and A, B, $R^2$ and $R^3$ are described below.

In summary, the compounds in accordance with the present invention can be represented by the following subgeneric formula:

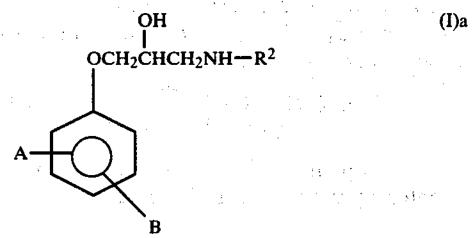

(I)a where $R^2$ is $C_1$ to $C_4$ linear or branched alkyl and A is hydrogen, halo, nitrile, $C_1$ to $C_2$ alkyl, $C_1$ to $C_2$ alkoxy, acetyl or propionyl and B is the group

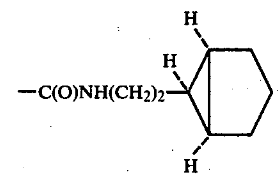

with the proviso that when group B is at the 4-position of the carbocyclic aryl ring, the substituent A is at position 2 or 3 of said ring, and when group B is at the 3 position of the carbocyclic aryl ring the substituent A is at position 4 or 6 of said ring.

In summary, the compounds in accordance with the present invention can be further represented by the following subgeneric formula:

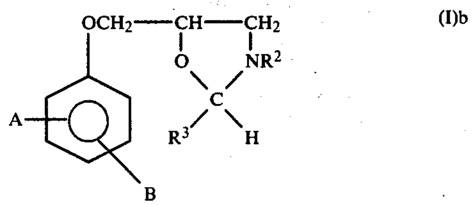

(I)b where A and B are defined above, $R^2$ is $C_1$ to $C_4$ linear or branched alkyl and $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ to $C_4$ linear or branched acyl, nitrile, nitro or $C_1$ to $C_4$ linear or branched carboalkoxy.

Also encompassed within the present invention are pharmaceutically acceptable salts of the above compounds.

The compounds of the present invention of formula Ia are prepared by treating the corresponding 1,2-epoxy-3-(3-or 4-[2-(endobicyclo[3.1.0]hex-6-yl)ethylaminocarbonyl]-phenoxy)propane with an alkylamine having the desired alkyl substituent. Alternatively, these compounds can be prepared by the hydrolysis of the corresponding compounds of the present invention of formula Ib.

The process of the invention for preparing the compounds of formula Ib comprises treating the compounds of formula Ia with the desired $R^3$ aldehyde.

The pharmaceutical compositions of the present invention include solutions and solids or powders comprising one or more of the compounds in accordance with the present invention in combination with a suitable pharmaceutical solution, e.g. sterile water, or pharmaceutically solid excipients.

A more detailed description of the present invention can be had by referring to the Description of the Preferred Embodiments hereinbelow.

DESCRIPTION OF PREFERRED EMBODIMENTS

The compounds of the present invention can be represented by the following formula

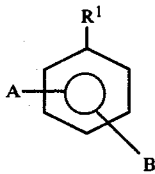

(I)

where $R^1$ is the radical

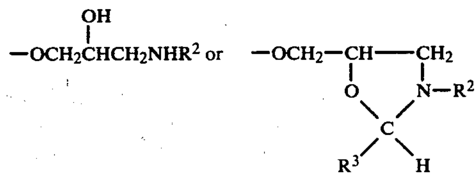

The compounds are more particularly represented by the formulas

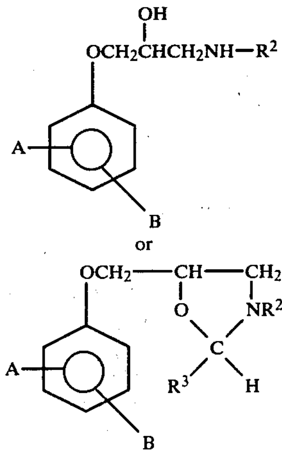

(I)a (I)b where A is hydrogen, halo, nitrile, $C_1$ to $C_2$ alkyl, $C_1$ to $C_2$ alkoxy, acetyl, or propionyl; B is the group

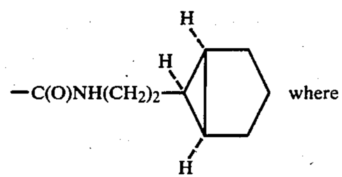

where $R^2$ is $C_1$ to $C_4$ linear or branched alkyl, $R^3$ is hydrogen, $C_1$ to $C_4$ linear or branched alkyl, or $C_6$ to $C_{10}$ carbocyclic aryl optionally substituted with halo, $C_1$ to $C_4$ linear or branched alkyl, $C_1$ to $C_4$ linear or branched alkoxy, $C_1$ to $C_4$ linear or branched carboalkoxy, $C_2$ to $C_4$ linear or branched acyl, nitrile or nitro, with the proviso that when group B is at the 4 position of the carbocyclic aryl ring, the substituent A is at position 2 or 3 of said ring and when group B is at the 3 position of the carbocyclic aryl ring, the substituent A is at position 4 or 6 of said ring.

The substituent on the carbocyclic aromatic ring, A, is illustrated by hydrogen, methyl, ethyl, methoxy, ethoxy, chloro, bromo, fluoro, nitrile, acetyl, propionyl. Preferably the substituent A is chloro, bromo, methyl, ethyl, methoxy or ethoxy.

The pharmaceutically acceptable salts of the above compounds are also encompassed within the present invention.

It should be noted that the above compounds bear the substituent endobicyclo[3.1.0]hex-6-yl ethylaminocarbonyl, e.g. Group B or

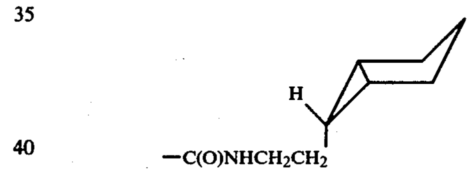

, where the open bond represents the point of attachment to the carbocyclic aryl ring.

The term pharmaceutically acceptable salts refers to those hydrogen anion addition salts which do not adversely affect the pharmaceutical properties of the parent compounds. With respect to the addition salts, suitable inorganic anions include, for example, chloride, bromide, iodide, sulfate, phosphate, nitrate, and the like. Suitable organic anions include for example, acetate, benzoate, lactate, picrate, propionate, butyrate, valerate, tartrate, maleate, fumarate, citrate, succinate, tosylate, ascorbate, nicotinate, adipate, gluconate and the like. Illustrations of the compounds of formula Ia can be had by reference to the examples. Typical Examples 1–3, 5 and 6 illustrative of the group $R^2$ includes methyl, ethyl, n-propyl, isopropyl, n-butyl, t-butyl and sec-butyl. Preferably $R^2$ is isopropyl or t-butyl.

The particularly preferred compounds of formula Ia in accordance with the present invention are:

1-isopropylamino-3-(4-[2-(endobicyclo[3.1.0]hex-6-yl)-ethylaminocarbonyl]phenoxy)-2-propanol;

1-t-butylamino-3-(4-[2-(endobicyclo[3.1.0]hex-6-yl)-ethylaminocarbonyl]phenoxy)-2-propanol;

1-isopropylamino-3-(2-chloro-4-[2-(endobicyclo[3.1.0]-hex-6-yl)ethylaminocarbonyl]phenoxy)-2-propanol;

1-t-butylamino-3-(2-chloro-4-[2-(endobicyclo[3.1.0]-hex-6-yl)ethylaminocarbonyl]phenoxy-2-propanol;

1-isopropylamino-3-(2-acetyl-4-[2-(endobicyclo[3.1.0]-hex-6-yl)ethylaminocarbonyl]phenoxy)-2-propanol;

1-t-butylamino-3-(2-acetyl-4-[2-(endobicyclo[3.1.0]-hex-6-yl)ethylaminocarbonyl]phenoxy)-2-propanol;

1-isopropylamino-3-(2-cyano-4-[2-(endobicyclo[3.1.0]-hex-6-yl)ethylaminocarbonyl]phenoxy)-2-propanol;

1-t-butylamino-3-(2-cyano-4-[2-(endobicyclo[3.1.0]-hex-6-yl)ethylaminocarbonyl]phenoxy)-2-propanol;

1-isopropylamino-3-(2-fluoro-4-[2-(endobicyclo[3.1.0]-hex-6-yl)ethylaminocarbonyl]phenoxy)-2-propanol;

1-t-butylamino-3-(2-fluoro-4-[2-(endobicyclo[3.1.0]-hex-6-yl)ethylaminocarbonyl]phenoxy)-2-propanol;

1-isopropylamino-3-(2-bromo-4-[2-(endobicyclo[3.1.0]-hex-6-yl)ethylaminocarbonyl]phenoxy)-2-propanol;

1-t-butylamino-3-(2-bromo-4-[2-(endobicyclo[3.1.0]-hex-6-yl)ethylaminocarbonyl]phenoxy)-2-propanol;

1-isopropylamino-3-(2-methyl-4-[2-(endobicyclo[3.1.0]-hex-6-yl)ethylaminocarbonyl]phenoxy)-2-propanol;

1-t-butylamino-3-(2-methyl-4-[2-(endobicyclo[3.1.0]-hex-6-yl)ethylaminocarbonyl]phenoxy)-2-propanol;

1-isopropylamino-3-(2-ethyl-4-[2-(endobicyclo[3.1.0]-hex-6-yl)ethylaminocarbonyl]phenoxy)-2-propanol;

1-t-butylamino-3-(2-ethyl-4-[2-(endobicyclo[3.1.0]-hex-6-yl)ethylaminocarbonyl]phenoxy)-2-propanol;

1-isopropylamino-3-(2-methoxy-4-[2-(endobicyclo[3.1.0]-hex-6-yl)ethylaminocarbonyl]phenoxy)-2-propanol;

1-t-butylamino-3-(2-methoxy-4-[2-(endobicyclo[3.1.0]-hex-6-yl)ethylaminocarbonyl]phenoxy)-2-propanol;

1-isopropylamino-3-(2-ethoxy-4-[2-(endobicyclo[3.1.0]-hex-6-yl)ethylaminocarbonyl]phenoxy)-2-propanol;

1-t-butylamino-3-(2-ethoxy-4-[2-(endobicyclo[3.1.0]-hex-6-yl)ethylaminocarbonyl]phenoxy)-2-propanol;

1-isopropylamino-3-(3-chloro-4-[2-(endobicyclo[3.1.0]-hex-6-yl)ethylaminocarbonyl]phenoxy)-2-propanol;

1-t-butylamino-3-(3-chloro-4-[2-(endobicyclo[3.1.0]-hex-6-yl)ethylaminocarbonyl]phenoxy)-2-propanol;

1-isopropylamino-3-(3-methyl-4-[2-(endobicyclo[3.1.0]-hex-6-yl)ethylaminocarbonyl]phenoxy)-2-propanol;

1-t-butylamino-3-(3-methyl-4-[2-(endobicyclo[3.1.0]-hex-6-yl)ethylaminocarbonyl]phenoxy)-2-propanol;

1-isopropylamino-3-(3-ethyl-4-[2-(endobicyclo[3.1.0]-hex-6-yl)ethylaminocarbonyl]phenoxy)-2-propanol;

1-t-butylamino-3-(3-ethyl-4-[2-(endobicyclo[3.1.0]-hex-6-yl)lethylaminocarbonyl]phenoxy)-2-propanol;

1-isopropylamino-3-(3-methoxy-4-[2-(endobicyclo[3.1.0]-hex-6-yl)ethylaminocarbonyl]phenoxy)-2-propanol;

1-t-butylamino-3-(3-methoxy-4-[2-(endobicyclo[3.1.0]-hex-6-yl)ethylaminocarbonyl]phenoxy)-2-propanol;

1-isopropylamino-3-(3-ethoxy-4-[2-(endobicyclo[3.1.0]-hex-6-yl)ethylaminocarbonyl]phenoxy)-2-propanol;

1-t-butylamino-3-(3-ethoxy-4-[2-(endobicyclo[3.1.0]-hex-6-yl)ethylaminocarbonyl]phenoxy)-2-propanol;

1-isopropylamino-3-(3-bromo-4-[2-(endobicyclo[3.1.0]-hex-6-yl)ethylaminocarbonyl]phenoxy)-2-propanol;

1-t-butylamino-3-(3-bromo-4-[2-(endobicyclo[3.1.0]-hex-6-yl)ethylaminocarbonyl]phenoxy)-2-propanol;

1-isopropylamino-3-(6-chloro-3-[2-(endobicyclo[3.1.0]-hex-6-yl)ethylaminocarbonyl]phenoxy)-2-propanol;

1-t-butylamino-3-(6-chloro-3-[2-(endobicyclo[3.1.0]-hex-6-yl)ethylaminocarbonyl]phenoxy)-2-propanol;

1-isopropylamino-3-(6-bromo-3-[2-(endobicyclo[3.1.0]-hex-6-yl)ethylaminocarbonyl)phenoxy)-2-propanol;

1-t-butylamino-3-(6-bromo-3-[2-(endobicyclo[3.1.0]-hex-6-yl)ethylaminocarbonyl)phenoxy)-2-propanol;

1-isopropylamino-3-(6-cyano-3-[2-(endobicyclo[3.1.0]-hex-6-yl)ethylaminocarbonyl]phenoxy)-2-propanol;

1-t-butylamino-3-(6-cyano-3-[2-(endobicyclo[3.1.0]-hex-6-yl)ethylaminocarbonyl]phenoxy)-2-propanol;

1-isopropylamino-3-(6-methyl-3-[2-(endobicyclo[3.1.0]-hex-6-yl)ethylaminocarbonyl]phenoxy)-2-propanol;

1-t-butylamino-3-(6-methyl-3-[2-(endobicyclo[3.1.0]-hex-6-yl)ethylaminocarbonyl]phenoxy)-2-propanol;

1-isopropylamino-3-(6-ethyl-3-[2-(endobicyclo[3.1.0]-hex-6-yl)ethylaminocarbonyl]phenoxy)-2-propanol;

1-t-butylamino-3-(6-ethyl-3-[2-(endobicyclo[3.1.0]-hex-6-yl)ethylaminocarbonyl]phenoxy)-2-propanol;

1-isopropylamino-3-(6-methoxy-3-[2-(endobicyclo[3.1.0]-hex-6-yl)ethylaminocarbonyl]phenoxy)-2-propanol;

1-t-butylamino-3-(6-methoxy-3-[2-(endobicyclo[3.1.0]-hex-6-yl)ethylaminocarbonyl]phenoxy)-2-propanol;

1-isopropylamino-3-(6-ethoxy-3-[2-(endobicyclo[3.1.0]-hex-6-yl)ethylaminocarbonyl]phenoxy)-2-propanol;

1-t-butylamino-3-(6-ethoxy-3-[2-(endobicyclo[3.1.0]-hex-6-yl)ethylaminocarbonyl]phenoxy)-2-propanol;

1-isopropylamino-3-(4-chloro-3-[2-(endobicyclo[3.1.0]-hex-6-yl)ethylaminocarbonyl]phenoxy)-2-propanol;

1-t-butylamino-3-(4-chloro-3-[2-(endobicyclo[3.1.0]-hex-6-yl)ethylaminocarbonyl]phenoxy)-2-propanol;

1-isopropylamino-3-(4-bromo-3-[2-(endobicyclo[3.1.0]-hex-6-yl)ethylaminocarbonyl]phenoxy)-2-propanol;

1-t-butylamino-3-(4-bromo-3-[2-(endobicyclo[3.1.0]-hex-6-yl)ethylaminocarbonyl]phenoxy)-2-propanol;

1-isopropylamino-3-(4-methyl-3-[2-(endobicyclo[3.1.0]-hex-6-yl)ethylaminocarbonyl]phenoxy)-2-propanol;

1-t-butylamino-3-(4-methyl-3-[2-(endobicyclo[3.1.0]-hex-6-yl)ethylaminocarbonyl]phenoxy)-2-propanol;

1-isopropylamino-3-(4-methoxy-3-[2-(endobicyclo[3.1.0]-hex-6-yl)ethylaminocarbonyl]phenoxy)-2-propanol;

1-t-butylamino-3-(4-methoxy-3-[2-(endobicyclo[3.1.0]-hex-6-yl)ethylaminocarbonyl]phenoxy)-2-propanol;

1-isopropylamino-3-(4-ethyl-3-[2-(endobicyclo[3.1.0]-hex-6-yl)ethylaminocarbonyl]phenoxy)-2-propanol; and 1-t-butylamino-3-(4-ethyl-3-[2-(endobicyclo[3.1.0]-hex-6-yl)ethylaminocarbonyl]phenoxy)-2-propanol.

Typical illustrations of the compounds of formula Ib can be had by reference to Examples 4 and 7. The preferred $R^2$ substituents are isopropyl and t-butyl. $R^3$ is preferably hydrogen, methyl, or phenyl optionally mono substituted with halo $C_1$ to $C_2$ alkyl, $C_1$ to $C_2$ alkoxy, $C_2$ to $C_3$ acyl, $C_1$ to $C_2$ carboalkoxy, nitrile or nitro.

The particularly preferred compounds of formula Ib in accordance with the present invention are:

2-phenyl-3-t-butyl-5-(4-[2-(endobicyclo[3.1.0]hex-6-yl)-ethylaminocarbonyl]phenoxymethyl)oxazolidine;

3-t-butyl-5-(4-[2-(endobicyclo[2.1.0]hex-6-yl)-ethylaminocarbonyl]phenoxymethyl)oxazolidine, and the like.

2-Phenyl-3-isopropyl-5-(4-[2-(endobicyclo[3.1.0]hex-6-yl)-ethylaminocarbonyl]phenoxymethyl)oxazolidine;

3-t-butyl-5-(4-[2-(endobicyclo[3.1.0]hex-6-yl)ethylaminocarbonyl]phenoxymethyl)oxazolidine;

3-isopropyl-5-(4-[2-(endobicyclo[3.1.0]hex-6-yl)ethylaminocarbonyl]phenoxymethyl)oxazolidine;

2-methyl-3-isopropyl-5-(4-[2-(endobicyclo[3.1.0]hex-6-yl)ethylaminocarbonyl]phenoxymethyl)oxazolidine;

2-methyl-3-t-butyl-5-(4-[2-(endobicyclo[3.1.0]hex-6-yl)ethylaminocarbonyl]phenoxymethyl)oxazolidine;

The preferred pharmaceutically acceptable salts are the hydrogen addition salts of bromide, sulfate, lactate, tartrate, succinate, and especially chloride and maleate. The preferred salts are the preferred anion addition salts of the compounds of formulas Ia or Ib in accordance with the present invention and correspondingly the particularly preferred salts are the preferred hydrogen-anion addition salts of the preferred and the particularly preferred compounds herein, and especially the hydrochloride and maleate salts.

The compounds in accordance with the present invention are conveniently prepared by applying the procedures discussed in the before referenced U.S. patent application Ser. No. 706,412 filed July 19, 1976 incorporated herein by reference.

Briefly, the initial reaction sequence for the preparation of the beta adrenergic blocking precursor (compound III) is as follows:

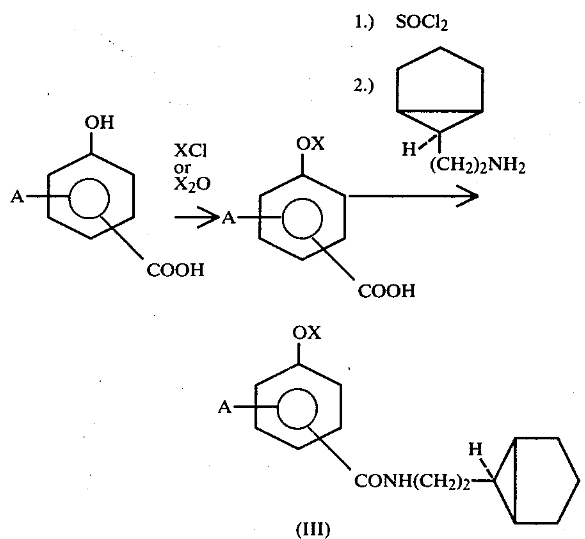

where X is $C_2$ to $C_4$ linear or branched acyl and A is defined above.

The above amide-forming reaction can be carried out by any of the well-known classical prior art procedures. Most conveniently, the amide is formed by first admixing the carboxylic acid with thionyl chloride in an aromatic solvent and heating to a temperature of about 70° C. The amine can then be added without isolating the intermediate acid chloride, giving the amide, compound (III). See for example Preparation 3.

The compounds in accordance with the present invention are prepared from the above precursor compound (III) by the following reaction scheme:

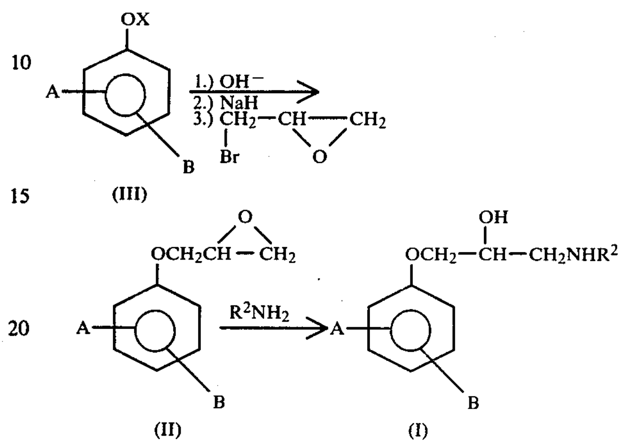

where X, A, B and $R^2$ are defined above. The formation of the oxirane adduct e.g., compound II is specifically illustrated herein in Preparation 5.

The above sequence can be effected by first treating the compound of formula (III) with strong base such as aqueous sodium hydroxide to remove the protecting group X. The resulting phenol is then typically reacted with an alkali metal hydride. This initial treatment is typically conducted at temperatures in the range of about from −30° to 30° C., preferably about from −10° to 5° C. for about from one minute to one hour, preferably about from five minutes to 20 minutes. An epihalohydrin such as epibromohydrin or epichlorohydrin typically dissolved in an inert organic solvent, can then be added to the preceding mixture. Typically, this treatment is conducted at temperatures in the range of about from 20° to 75° C., preferably about from 25° to 45° C., for about from one minute to three hours, preferably about from 10 to 30 minutes. Typically, mole ratios of alkali metal hydride:phenol [i.e where X=H in compound (III)] of about from 1 to 5:1 are used, preferably about from 1.0 to 1.3:1, and mole ratios of compound of formula (III) (i.e. where X=H):epihalohydrin in the range of about from 1 to 5:1 preferably about from 1.0 to 1.3:1 are used. Suitable alkali metal hydrides which can be used include, for example, sodium hydride, potassium hydride, lithium hydride, and the like. Suitable inert organic solvents which can be used include, for example, tetrahydrofuran, diethyl ether, dioxane, dimethoxyethane, dimethylformamide and the like, and mixtures thereof. Both procedures of the treatment are conducted under anhydrous conditions, and preferably under an inert atmosphere (e.g. nitrogen). Intermediate compound (II) is preferably isolated before being used as starting material for the next step. Such isolation can be effected by conventional separation procedures such as, for example, precipitation with water, extraction, crystallization or chromatography. Specific illustrations of typical separation and isolation procedures can be had by reference to the appropriate Preparation, hereinbelow.

The compounds of formula (I)a can be conveniently prepared by treating compound (II) with a monoalkylamine having the desired alkyl substituent. Typically, this treatment is conducted in an inert organic solvent and is typically conducted at temperatures in the range of about from −10° to 100° C., preferably about from 10° to 50° C., for about from one hour to 48 hours, preferably about from three to 18 hours. Typically, a mole ratio of alkylamine:compound (II) is in the range of about from one to 30:1, preferably about from one to 10:1, is used. Suitable alkylamines which can be used include, for example, methylamine, ethylamine, isopropylamine, t-butylamine, and the like. Suitable inert organic solvents which can be used include, for example, methanol, ethanol, monoglyme, and the like and mixtures thereof. The resulting products of formula (I)a can then be separated and isolated according to conventional procedures such as, for example, evaporation, crystallization, chromatography, thin-layer chromatography, etc. Specific illustrations of typical separation and isolation procedures can be had by reference to the corresponding examples, set forth hereinbelow.

The compounds of formula Ib can be prepared directly from the corresponding compounds of formula Ia as follows:

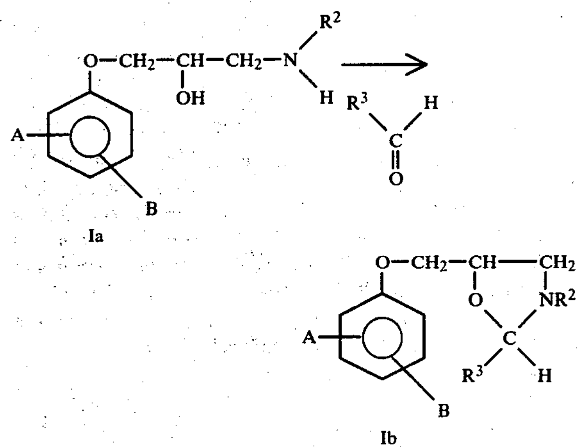

wherein $R^2$, $R^3$, A and B are as defined hereinabove.

This preparation can be conveniently effected by treating the corresponding compound of formula Ia with an aldehyde having the desired $R^3$ substituent. The reaction can be effected by simply treating the compound of formula Ia with the desired aldehyde using a lower alkanol (e.g. ethanol) as solvent. Typically a mole ratio of about from one to 10 moles of aldehyde is used per mole of formula Ia. The reactions are typically conducted at temperatures in the range of about from 20° to 140° C. for about from one to 48 hours. Suitable aldehydes which can be used include, for example formaldehyde, acetaldehyde, benzaldehyde, p-acetylbenzaldehyde, p-cyanobenzaldehyde, p-chlorobenzaldehyde, p-carbomethoxybenzaldehyde and the like. In some cases, a strong base is desirably present in the reaction mixture such as aluminum isopropoxide and the like. Alternately, these compounds are prepared by heating a mixture of the desired $R^3$ aldehyde and the compounds of formula Ia in an inert organic solvent such as benzene, toluene, etc. and azeotropically removing water.

Alternatively, the oxazolidine compounds in accordance with the present invention, compound Ib can be prepared by the following reaction:

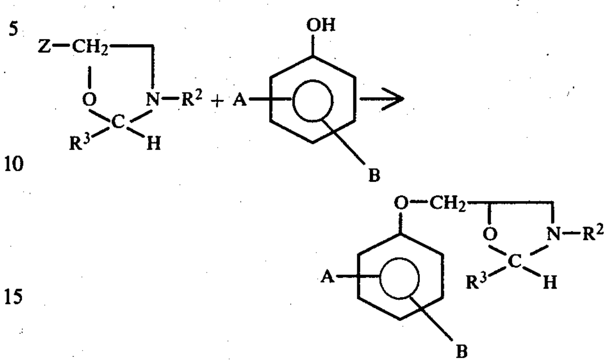

where Z is any readily displaceable group such as halo, mesyloxy, toxyloxy and the like and A, B $R^2$ and $R^3$ are described above.

This reaction is conveniently carried out by first treating the 5-hydroxymethyl-3-alkyl 2-optionally substituted oxazolidine with a reagent that will react with the hydroxy moiety of the 5-hydroxymethyl thereby forming an intermediate bearing a 5-methyl-leaving group-substituted oxazolidine (the group Z). Such displaceable leaving groups are well known in the prior art, e.g., the reactions of alcohols with the selected reagents to yield leaving group-substituted intermediates. See for example Fieser & Fieser, Reagents for Organic Synthesis, page 662 (1967) and Example 7 herein. Preferably the leaving group Z is tosyloxy or mesyloxy. After isolation of the Z-substituted oxazolidine, the displacement is affected by subsequent reaction with the desired A and B substituted phenolic anion to yield the oxazolidine compound Ib. Typically, the leaving group-substituted oxazolidine is formed by reaction of methanesulfonyl chloride or p-toluenesulfonylchloride with the oxazolidine alcohol in the presence of an acid acceptor-containing solution. Typical acid acceptors are the trialkyl- or arylamines or alkali metal carbonates. The subsequent reaction with the phenol is accomplished by first activating the phenol typically with an alkali metal hydride such at temperatures of about −10° to about 100° preferably 0° to 30° C. for about one minute to about 1 hour preferably five minutes to 20 minutes. The oxazolidine dissolved in a mixture allowed to organic solvent is next added and the solutions allowed to react at from about 25° to about 100° C. preferably 70° to 90° C. for about 1 hour to about 8 hours preferably 1 hour to 3 hours. Typically the ratio of 5-hydroxymethyl-substituted oxazolidine: leaving group reagent is in the range 1 to 5:1, preferably 1 to 1.5:1. The ratio of 5-leaving group-substituted oxazolidine:A and B substituted phenol:alkali metal hydride is in the range 1 to 5:1:1 to 2 preferably 1.3:1:1.1.

The product of formula Ib can be separated and purified according to conventional procedures such as, for example, illustrated in Examples 6 or 7, hereinbelow. Care should be exercised during the purification procedure as the compounds of formula Ib are easily hydrolyzed to the compounds of formula Ia under both acid and basic conditions. The alkylamino compounds of formula Ia can be readily prepared by simple acid or base hydrolysis of the corresponding compounds of formula Ib. Acid hydrolysis can be conveniently effected by treating the compound of formula Ib with a suitable organic acid such as, for example, acetic acid, formic acid, oxalic acid and the like or a suitable inorganic acid such as, for example, hydrochloric acid, sulfuric acid and the like. Preferably this hydrolysis is conducted under mildly acidic conditions. Similarly, basic hydrolysis can be conducted by treating the compound of formula Ib with a suitable base such as, for example, dilute sodium hdyroxide. Preferably this hydrolysis is conducted under mildly alkaline conditions. Alternatively, the hydrolysis can be conducted via exchange with a suitable ion exchange resin in either the $H^+$ or $OH^-$ form.

The pharmaceutically acceptable acid addition salts of the compounds of formulas Ia and Ib can be prepared from the parent compound, via careful neutralization, with the desired acid. Other pharmaceutically acceptable addition salts can then be conveniently prepared from the addition salts via anion exchange with a suitable ion exchange resin in the desired anionic form.

The compounds of the invention are useful in the treatment and palliation of cardiovascular abnormalities in mammals. These compounds primarily achieve their therapeutic action by selectively blocking the cardiac beta-adrenergic receptor sites and, accordingly, because they are cardiac selective, they can also be applied to treat cardiac abnormalities in patients suffering from asthma or chronic obstructive lung disease.

The compounds are especially useful in the treatment or palliation of cardiac arrhythmias, angina pectoris, hypertrophic subaortic stenosis, pheochromocytoma, thyrotoxicosis, hyperkenetic syndromes, tetralogy of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication presently commonly used (i.e. nitroglycerin) in the treatment of angina pectoris has no recognized prophylactic action. Additional information concerning the use, action and determination of beta-blockers can be obtained by reference to the literature such as, for example, Dotlery et al, *Clinical Pharmacology and Therapeutics,* Volume 10, No. 6, 765–797 and the references cited therein.

The compounds of the invention are also useful in the treatment of hypertension in mammals.

The compounds of this invention are typically administered, both for the treatment of cardiac disorders and hypertension, in dosages of about from 0.01 to 5 mg per kg. of body weight. The precise effective dosage will, of course, vary depending upon the mode of administration, the condition being treated and the host. Where the compounds are used to treat cardiac conditions such as arrhythmias, the compounds are typically administered either orally or intravenously. Where the compounds are administered to treat hypertension or cardiac conditions such as angina pectoris, the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula Ia, the compounds are typically administered as pharmaceutically acceptable salts. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs and optionally can contain small quantities of preservatives and/or buffering agents, and preferably contain the therapeutic agent in convenient unit dosage concentrations.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful local anesthetic activity. Where the compounds are supplied as local anesthetics, they can be administered topically; intradermally; or subcutaneously.

A further understanding of the invention can be had from the following non-limiting Preparations and Examples. Also as used hereinabove and below unless expressly stated to the contrary, all temperatures and temperature ranges refer to the Centigrade system and the terms ambient or room temperature refer to about 20° C. The term percent or (%) refers to weight percent and the term mole or moles refers to gram moles. The term equivalent refers to a quantity of reagent equal in moles to the moles of the preceding or succeeding reactant recited in that Preparation or Examples in the terms of moles or finite weight or volume. Proton or $^{13}$carbon nuclear magnetic reasonance spectra (NMR and $^{13}$C NMR) are determined at 100, 90, or 60 MHz (the signs of the coupling constants are not assigned) and signals are assigned as singlets (s), broad singlets (bs) doublets (d), double doublets (dd), triplets (t), double triplets (dt), quarters (q) and multiplets (m) and reported using the $\delta$ scale from tetramethylsiland (internal standard) unless as otherwise noted. Compounds having assymetric centers and optical activity are isolated in their racemic form (±) unless otherwise indicated.

PREPARATION 1

2-(Endobicyclo[3.1.0]hex-6-yl)ethylamine a. In this preparation 1.9 g. (0.05 mole) of lithium aluminum hydride is dissolved in 100 ml. of diethyl ether, under nitrogen, cooled to 0° C., and then 10.8 g. (0.1 mole) of endobicyclo[3.1.0]hex-2-en-6-yl carboxaldehyde in 100 ml. of diethyl ether is added dropwise. The mixture is allowed to warm to room temperature, and then stirred for 30 minutes. Ten milliliters of ethyl acetate are added, and then 10 ml. of water. The mixture is then filtered and the filtrate dried with anhydrous magnesium sulfate, filtered, and the filtrate evaporated under vacuum affording 6-(hydroxymethyl)-endobicyclo[3.1.0]hex-2-ene.

b. A mixture containing 10 g. (0.091 mole) of 6-(hydroxymethyl)-endobicyclo[3.1.0]hex-2-ene and 0.5 g. of 5% platinum on carbon in 250 ml. of ethyl acetate is stirred under hydrogen, at room temperature, until no further hydrogen is absorbed (about two liters is absorbed). The catalyst is filtered off and the filtrate evaporated under vacuum affording 6-(hydroxymethyl)-endobicyclo[3.1.0]hexane.

c. Ten grams (0.089 mole) of 6-(hydroxymethyl)-endobicyclo[3.1.0]hexane are mixed with 23.4 g. (0.089 mole) of triphenylphosphine in 40 ml. of carbon tetrachloride and heated, under nitrogen, at 60° C. for four hours. The mixture is then poured into 200 ml. of hexane, stirred, and then filtered and the filtrate concentrated by evaporation under vacuum. The concentrate is then chromatographed on silica gel, eluting the 5% ethyl acetate-95% (vol.) hexane, affording 6-(chloromethyl)-endobicyclo[3.1.0]hexane.

d. A mixture containing 9 g. (0.069 mole) of 6-(chloro-methyl)-endobicyclo[3.1.0]hexane and 4.9 g. (0.1 mole) of sodium cyanide in 100 ml. of dimethylsulfoxide is heated at 70° C., under nitrogen, for four hours, and then poured into 500 ml. of methylene chloride. The mixture is then washed three times with water, dried over anhydrous magnesium sulfate, and filtered. The filtrate is evaporated under vacuum and the resulting residue then chromatographed on silica gel, eluting with 5% ethyl acetate-95% (vol.) hexane affording endobicyclo[3.1.0]hex-6-yl acetonitrile.

e. 2.2 Grams (0.058 mole) of lithium aluminum hydride are dissolved in 100 ml. of anhydrous diethyl ether at 0° C., under nitrogen, and 7 g. (0.058 mole) of endobicyclo[3.1.0]hex-6-yl acetonitrile in 100 ml. of diethyl ether is added dropwise. The mixture is maintained at 0° C. for 30 minutes and then 10 ml. of water is carefully added and the resulting mixture filtered. The filtrate is dried over potassium hydroxide pellets, filtered, and the filtrate distilled to remove the ethyl ether solvent, affording 2-(endobicyclo[3.1.0]hex-6-yl)ethylamine.

PREPARATION 2

4-Hydroxy-3-acetylbenzoic acid

A solid mixture of 15 g. of methyl 4-acetoxy-benzoate and 17.5 g. of aluminum chloride in a beaker is heated by oil bath to 148°-150°, with stirring for about 15 minutes. (The mixture liquified and resolidified). The mixture is removed from the oil bath, added to 100 ml. concentrated hydrochloric acid, and diluted with 100 ml. of water. The precipitate is filtered, washed with water and dissolved in aqueous 10% sodium hydroxide solution. The solution is filtered to remove insolubles. Acidification of the filtrate with concentrated hydrochloric acid causes precipitation of a mixture of 4-hydroxy-3-acetylbenzoic acid and 4-hydroxy-benzoic acid (9.0 g.). Crystallization from methanol water affords the pure 4-hydroxy-3-acetylbenzoic acid, 2.5 g.

PREPARATION 3

4-Hydroxy-3-cyano benzoic acid a. A solution of 15 g. of ethyl 4-nitrobenzoate and 15 g. of potassium cyanide in 200 ml. of dimethyl sulfoxide (DMSO) is heated at 100° for 3 hours. Most of the DMSO is distilled (at 1 mm Hg), water (100 ml.) is added and the water solution extracted twice with ethyl acetate (100 ml. each). This ethyl acetate solution is discarded and the water layer acidified with hydrochloric acid. Extraction of the acid solution with ethyl acetate and chromatography of the mixture over silica gel affords 5.9 g. of the ethyl 4-hydroxy-3-cyanobenzoate. See Chem. Comm., 1971, 1121.

b. A solution of the compound of part a. (above) in methanol (90 ml.) is treated with 100 ml. aqueous 10% sodium hydroxide solution at room temperature for 30 minutes. The basic solution is made acidic with hydrochloric acid. The precipitated 4-hydroxy-3-cyano benzoic acid, is filtered, washed with $H_2O$ and dried giving 4.9 g. 4-hydroxy-3-cyano benzoic acid. $^{13}C$ NMR in $CD_3OD$ 168.04 COOH
165.31 1 (carbon number)
137.12 5 (carbon number)
136.80 3 (carbon number)
123.93 4 (carbon number)
117.06 6 (carbon number)
117.06 C≡N
101.14 2 (carbon number)

PREPARATION 4 a. 4-Acetoxy-3-chlorobenzoic acid

A mixture of 10 g. 4-hydroxy-3-chlorobenzoic acid and 50 ml. of acetic anhydride is refluxed for two hours. Excess acetic anhydride is distilled under vacuum and the residue diluted and stirred with a mixture of methanol (100 ml.) and water (20 ml.) at about 50° for 30 minutes. The mixture is then reduced to low volume under vacuum, water added and the precipitated crystals filtered. Recrystallization from toluene gives 6.5 g. (52% yield) m.p. 162°-163° C.

b. 4-Acetoxy-3-acetylbenzoic acid

To a suspension of 2.3 g. of 4-hydroxy-3-acetylbenzoic acid in 100 ml. of methylene chloride and 100 ml. of tetrahydrofuran, a mixture of 1.5 g. of triethylamine, 1.6 g. of 4-N-dimethylaminopyridine and 1.5 g. of acetic anhydride is added. The reaction mixture is heated at 50° for one hour. The solution is extracted with ethyl acetate, the organic layer washed with water and dilute hydrochloric acid and evaporated to dryness to yield 2.1 g. of the benzoic acid product. NMR in $CDCl_3$ 2.37 (s, 3H, $-OCOCH_3$)
2.62 (s, 3H $-COCH_3$)
7.24 (d, 1H, J=8.5 H2, H6)
8.25 (dd, 1H, J=8.5 2.0 H2, H5)
8.52 (d, 1H, J=2.0, H3)

c. 4-Acetoxybenzoic acid

A solution of 20 g. of 4-hydroxybenzoic acid in 200 ml. of benzene and 40 ml. of acetyl chloride is refluxed for 3 hours. Solvent and excess acetyl chloride are evaporated. The mixture is dissolved in methanol (150 ml.) and water (20 ml.) added; after 15 minutes, addition of more water results in the precipitation of 4-acetoxy benzoic acid, m.p. 192°-193° C.

PREPARATION 5

2-Chloro-4-[2-(endobicyclo[3.1.0]hex-6-yl)ethylcarbonyl]phenylacetate

A mixture of 15 ml. of thionyl chloride, 2.15 g. of 4-acetoxy-3-chlorobenzoic acid (Preparation 4a) in 150 ml. of toluene is stirred at 70° for 3 hours under nitrogen, the solvent removed under vacuum and the residue pumped to dryness. The residue is dissolved in dry tetrahydrofuran (150 ml.) and a mixture of triethylamine (3 ml.) and 2-(endobicyclo[3.1.0]hex-6-yl)ethylamine (1.38 g., 0.011 mole) is added dropwise with stirring at room temperature. After stirring for 2 hours the mixture is poured into ethyl acetate (300 ml.), washed twice with a saturated sodium chloride solution, dried over magnesium sulfate, filtered and the solvent removed under vacuum. After chromatographing the residue on silica gel and eluting with 50% ethyl acetate-50% hexane, the acetate is isolated, yielding 1.6 g. (50%) m.p. 101°-102° C.

Similarly by following the same procedure above but using substituents other than 2-chloro on the $C_6$ carbocyclic aryl ring, the following are prepared:

4-[2-(endobicyclo[3.1.0]hex-6-yl)ethylaminocarbonyl]phenyl acetate; NMR in $CDCl_3$ 0.4–2.0 (m, 11H; CH and $CH_2$'s)

2.32 (s, 3H, $CH_3$)

3.52 (q, 2H, J=6.5 H2; —$NCH_2$—)

7.18 (typical AA'BB' of p-disubstituted benzene $J_{AB}$~8.5 H2)

7.83 (typical AA'BB' of p-disubstituted benzene $J_{AB}$~8.5 H2)

2-acetyl-4-[2-(endobicyclo[3.1.0]hex-6-yl)ethylaminocarbonyl]phenyl acetate;

2-cyano-4-[2-(endobicyclo[3.1.0]hex-6-yl)ethylaminocarbonyl]phenyl acetate;

3-cyano-4-[2-(endobicyclo[3.1.0]hex-6-yl)ethylaminocarbonyl]phenyl acetate;

3-acetyl-4-[2-(endobicyclo[3.1.0]hex-6yl)ethylaminocarbonyl]phenyl acetate; and 3-chloro-4-[2-(endobicyclo[3.1.0]hex-6-yl)ethylaminocarbonyl]phenyl acetate.

PREPARATION 6

2-Chloro-4-[2-(endobicyclo[3.1.0]hex-6-yl)ethylaminocarbonyl]phenol

A mixture of 1.6 g. of the acetate of Preparation 5, 1.6 g. of sodium hydroxide, 100 ml. of dimethoxyethane in 20 ml. of water is stirred for 30 minutes at room temperature and the solvents reduced to low volume under reduced pressure. Ethyl acetate (100 ml.) is added and the solution washed with water. The washed solution is dried over anhydrous magnesium sulfate, filtered and the solvent removed to yield the liquid phenolic product in 1.4 g. (~100%), NMR in $CDCl_3$ 0.55–2.15 (m, 11H, CH and $CH_2$)

3.55 (dd, 2H, J=6.5, $NCH_2$)

7.08 (d, 1H, J=8.5 Aromatic-H)

7.63 (dd, 1H, J=2,8.5 Aromatic-H)

7.85 (d, 1H, J=2, Aromatic-H)

Similarly, by following the same procedure above but using compounds bearing substituents other than chlorine on the carbocyclic aryl ring, the following compounds are prepared:

2-cyano-4-[2-(endobicyclo[3.1.0]hex-6-yl)ethylaminocarbonyl]phenyl; NMR in DMSO 0.55–1.9 (m, 11H, CH and $CH_2$)

3.25 (9, 2H, J=6.5, $NCH_2$)

3–4 (broad, 1H, OH)

7.05 (d, 1H, J=8.5, Aromatic-H)

7.97 (dd, 1H, J=2.5, 8.5, Aromatic-H)

8.10 (d, 1H, J=2.5, Aromatic-H)

8.20 (broad, 1H, NH)

2-acetyl-4-[2-(endobicyclo[3.1.0]hex-6-yl)ethylaminocarbonyl]phenol;

3-cyano-4-[2-(endobicyclo[3.1.0]hex-6-yl)ethylaminocarbonyl]phenol;

3-acetyl-4-[2-(endobicyclo[3.1.0]hex-6-yl)ethylaminocarbonyl]phenol; and 3-chloro-4-[2-(endobicyclo[3.1.0]hex-6-yl)ethylaminocarbonyl]phenol;

4-[2-(endobicyclo[3.1.0]hex-6-yl)ethylaminocarbonyl]phenol.

PREPARATION 7

1,2-Epoxy-3-(2-chloro-4-[2-(endobicyclo[3.1.0]hex-6-yl)ethylaminocarbonylphenoxy)propane Sodium hydride (0.25 g.) and 1.4 g. of the phenol of Preparation 4 are first mixed with stirring in dry dimethylformamide (50 ml.) under $N_2$, for 5 minutes. Epichlorohydrin, 0.84 g., is added and the mixture then warmed to 50° for 30 minutes. The solvent is removed under reduced pressure and the residue dissolved in ethyl acetate (250 ml.), washed twice with 50 ml. portions of water, dried over anhydrous magnesium sulfate, filtered and evaporated. The oily residue is chromatographed on silica gel, and eluted with 50% ethyl acetate/hexane. Crystallization of the product from ethyl acetate/hexane yields the white solid epoxide, m.p. 106°-108° C., yield-1.2 g. (71%).

Similarly, by following the same procedure above but using other substituted phenols, the following compounds are prepared:

1,2-epoxy-3-(4-[2-endobicyclo[3.1.0]hex-6-yl)ethylaminocarbonyl]phenoxy)propane, m.p. 89°-90° C.;

1,2-epoxy-3-(2-acetyl-4-[2-(endobicyclo[3.1.0]hex-6-yl)ethylaminocarbonyl)phenoxy)propane;

1,2-epoxy-3-[2-cyano-4-[2-(endobicyclo[3.1.0]hex-6-yl)ethylaminocarbonyl]phenoxy)propane; NMR in $CDCl_3$ 0.5–2 (m, 11H, CH and $CH_2$)

2.85 (m, 2H, epoxide $CH_2$)

3.5 (m, 3H, epoxide-CH and N-$CH_2$)

4.25 (m, 2H, —$OCH_2$—)

6.20 (broad, 1H, NH)

7.5 (d, 1H, J=8.5, Aromatic-H)

7.95 (dd and dd, 2H, Aromatic-H)

1,2-epoxy-3-(3-cyano-4-[2-(endobicyclo[3.1.0]hex-6-yl)ethylaminocarbonyl]phenoxy)propane;

1,2-epoxy-3-(3-acetyl-4-[2-(endobicyclo[3.1.0]hex-6-yl)ethylaminocarbonyl]phenoxy)propane;

1,2-epoxy-3-(3-chloro-4-[2-(endobicyclo[3.1.0]hex-6-yl)ethylaminocarbonyl]phenoxy)propane.

EXAMPLE 1

This example is illustrative of the process for preparing the compounds of the present invention.

(±) 1-isopropylamino-3-(4-[2-(endobicyclo[3.1.0-]hex-6-yl)ethylaminocarbonyl]phenoxy)-2-propanol.

To a solution of 1.9 g. of 1,2-epoxy-3-(4-[2-(endobicyclo[3.1.0]hex-6-yl)ethylaminocarbonyl]phenoxy)propane (Preparation 7) in 10 ml. of methanol is added 10 ml. of isopropylamine. The mixture is stirred at room temperature for 20 hours. The propanol product is isolated via preparative TLC plates, giving 1.7 g., m.p. 110°-111°. Using the epoxides illustrated in Preparation 7, the following propanol products are prepared in the manner similar to that disclosed above utilizing isopropylamine and t-butylamine respectively. All compounds were isolated in the racemic (±) form.

1-t-butylamino-3-(4-[2-(endobicyclo[3.1.0]hex-6-yl)ethylaminocarbonyl]phenoxy-2-propanol, m.p. 116°–117° C., 1-isopropylamino-3-(2-acetyl-4-[2-(endobicyclo[3.1.0]hex-6-yl)ethylaminocarbonyl]phenoxy)-2-propanol, m.p. 125°–127° C. (HCl), 1-t-butylamino-3-(2-acetyl-4-[2-(endobicyclo[3.1.0-]hex-6-yl)ethylaminocarbonyl]phenoxy)-2-propanol, 1-isopropylamino-3-(2-cyano-4-[2-(endobicyclo[3.1.0]hex-6-yl)ethylaminocarbonyl]phenoxy)-2-propanol,

| CARBON NUMBERS | |
|---|---|
| 165.73 } | 1' & C=O |
| 161.86 } | |
| 134.00 } | 3' 5' |
| 133.13 } | |
| 128.28 | 4' |
| 115.93 | C≡N |
| 112.81 | 6' |
| 101.53 | 2' |
| 71.13 | 1'' |
| 65.57 | 2'' |
| 51.82 | 4'' |
| 47.46 | 3'' |
| 41.09 | 8 |
| 27.11 | 3 |
| 25.23 | 2,4 |
| 24.02 | 7 |
| 22.30 | 1,5 |
| 21.07 } | 5'' |
| 19.14 } | 5''' |
| 19.08 | 6 |

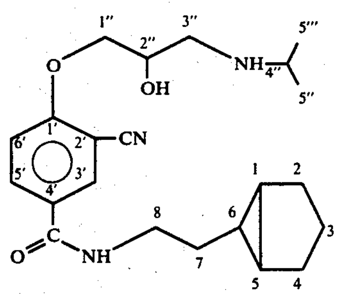

1-t-butylamino-3-(2-cyano-4-[2-(endobicyclo[3.1.0-]hex-6-yl)ethylaminocarbonyl]phenoxy)-2-propanol, 1-isopropylamino-3-(3-cyano-4-[2-(endobicyclo[3.1.0]hex-6-yl)ethylaminocarbonyl]phenoxy)-2-propanol, 1-t-butylamino-3-(3-cyano-4-[2-(endobicyclo[3.1.0-]hex-6-yl)ethylaminocarbonyl]phenoxy)-2-propanol, 1-isopropylamino-3-(3-acetyl-4-[2-(endobicyclo[3.1.0]-hex-6-yl)ethylaminocarbonyl]phenoxy)-2-propanol, 1-t-butylamino-3-(3-acetyl-4-[2-(endobicyclo[3.1.0]-hex-6-yl)-ethylaminocarbonyl]phenoxy)-2-propanol, 1-isopropylamino-3-(3-chloro-4-[2-(endobicyclo[3.1.0]-hex-6-yl)ethylaminocarbonyl]phenoxy)-2-propanol, 1-t-butylamino-3-(3-chloro-4-[2-(endobicyclo[3.1.0]-hex-6-yl)ethylaminocarbonyl]phenoxy)-2-propanol, 1-isopropylamino-3-(2-chloro-4-[2-(endobicyclo[3.1.0]-hex-6-yl)ethylaminocarbonyl]phenoxy)-2-propanol, 1-t-butylamino-3-(2-chloro-4-[2-(endobicyclo[3.1.0]-hex-6-yl)ethylaminocarbonyl]phenoxy)-2-propanol.

EXAMPLE 2

This example illustrates methods of preparing hydrochloride addition salts of the compounds of formula Ia. In this example 1 g. of 1-isopropylamino-3-(4-[2-(endobicyclo-[3.1.0]hex-6-yl)ethylaminocarbonyl]phenoxy)-2-propanol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with ethyl ether and then crystallized from methanol/diethyl ether, affording crystalline 1-isopropylamino-3-(4-[2-(endobicyclo[3.1.0]hex-6-yl)ethylaminocarbonyl]phenoxy)-2-propanol hydrochloride.

Similarly, by following the same procedure, the corresponding hydrochloride addition salts of each of the products of Examples 1 and 2 are respectively prepared.

EXAMPLE 3

This example illustrates methods of preparing the maleate addition salts of compounds of formula Ia. In this example one gram of 1-isopropylamino-3-(4-[2-(endobicyclo[3.1.0]-hex-6-yl)ethylaminocarbonyl]phenoxy)-2-propanol is dissolved in a solution of 5 ml. of ethyl ether and 5 ml. of ethanol at 20° C. To this solution is added 10 ml. of a saturated solution of maleic acid in ethyl ether. The mixture is allowed to stand for one hour at room temperature. The resulting precipitate is recovered by filtration, washed three times with ethyl ether and then crystallized from a mmixture of ethyl ether and ethanol (1:1) affording crystalline 1-isopropylamino-3-(4-[2-endobicyclo[3.1.0]hex-6-yl)ethylaminocarbonyl]

Similarly, by following the same procedure, the corresponding maleate salts of each of the products of Example 1 are prepared.

EXAMPLE 4

This example illustrates the method of converting the compounds of formula Ia into the corresponding compounds of formula Ib. In this example 1 mmole of 1-isopropylamino-3-(4-[2-(endobicyclo[3.1.0]hex-6-yl)ethylaminocarbonyl]phenoxy)-2-propanol in 10 ml. of methanol is admixed with 20 ml. of acetaldehyde and 2 g. of aluminum isopropoxide and then stirred at room temperature for one hour. The solvent is then removed by evaporation under vacuum affording 2-methyl-3-isopropyl 5-(4-[2-(endobicyclo[3.1.0]hex-6-yl)ethylaminocarbonyl]phenoxy)methyloxazolidine.

Similarly by following the same procedure but using other aldehydes in place of acetaldehyde, the corresponding 2-substituted 3-isopropyl)oxazolidine homologs of the above products are respectively prepared. By replaceing the above compound of Formula Ia with other Formula Ia compounds the compounds of Formula Ib can be prepared with various 3 substitutions on the oxazolidine ring.

EXAMPLE 5

This example illustrates the method of converting the compounds of Formula Ib into the compounds of Formula Ia of the invention. In this example 1 g. of 2-phenyl-3-t-butyl-5-(4-[2-(endobicyclo[3.1.0]hex-6-yl)ethylaminocarbonyl]phenoxymethyl)oxazolidine is dissolved in 50 ml. of ethyl acetate and this solution is treated with aqueous 5% sodium hydroxide (20 ml.) at 20° C. The mixture is allowed to stand, with shaking for 0.5 hours, the organic layer separated, washed three times with water, dried over magnesium sulfate and then evaporated to dryness affording 1-5-butylamino-3-(4-[2-(endobicyclo[3.1.0]hex6-yl)ethylaminocarbonyl]-phenoxy)-2-propanol.

Similarly, by following the same procedure, the products of Example 4 are respectively hydrolyzed to the corresponding compounds of Formula Ia.

EXAMPLE 6

This example illustrates an alternate method for converting the compounds of Formula Ib to the compounds of Formula Ia. In this example 1 g. of 2-phenyl-3-t-butyl-5-(4-[2-(endobicyclo[3.1.0]hex-6-yl)ethylaminocarbonyl]phenoxymethyl)oxazolidine is dissolved in 20 ml. of methanol containing 4 ml. of 5% aqueous hydrochloric acid at 20° C. After 30 minutes, the mixture is neutralized with dilute aqueous sodium carbonate solution, poured into water and extracted with ethyl acetate. The ethyl acetate extract is evaporated to dryness yielding 1-t-butylamino-3-(4-[2-(endobicyclo[3.1.0]hex-6-yl)ethylaminocarbonyl]phenoxy)-2-propanol.

EXAMPLE 7

This example illustrates an alternate method for the preparation of the compounds Ib:

2-phenyl-2-t-butyl-5-(4-[2-endobicyclo[3.1.0]hex-6-yl)ethylaminocarbonyl]phenoxymethyl)oxazolidine, (a) 2-phenyl-3-t-butyl-5-p-toluenesulfonyloxymethyloxazolidine.

To a solution of dl-2-phenyl-3-t-butyl-5-hydroxymethyloxazolidine (12.05 g.) in triethylamine (120 ml.) 13 is added p-toluenesulfonylchloride (14.5 g.). After 6 days at room temperature the mixture is added to water (500 ml.) and extracted with ether (2×200 ml.). The ether solution is washed with water, dried with anhydrous magnesium sulfate and evaporated to dryness. The residue is recrystallized from hexane to afford 2-phenyl-3-t-butyl-5-p-toluenesulfonyloxymethyloxazolidine.

Also prepared by the above technique, but substituting the desired oxazolidine for the dl-2-phenyl-3-t-butyl-5-p-toluenesulfonyloxymethyloxazolidine are:

3-t-butyl-5-p-toluenesulfonyloxymethyloxazolidine, m.p. 69°-70° C.

2-methyl-3-t-butyl-5-p-toluenesulfonyloxymethyloxazolidine.

(b) A sodium hydride [(57%) dispersion in mineral oil] (90 mg.) is washed with pentane 3 times and treated with 5 ml. of dry DMF. To the resulting suspension is added 490 mg. of 4-[2-(endobicyclo[3.1.0]hex-6-yl)ethylaminocarbonyl]-phenol dissolved in 15 ml. of DMF. After 10 minutes, 782 mg. of 2-phenyl-3-t-butyl-5-p-toluenesulfonyloxymethyloxazolidine (step a) in 5 ml. of DMF are added and the temperature of the reaction mixture raised to approximately 80° C. Stirring is continued for 2 hours. The reaction mixture is cooled, poured into 50 ml. of water, and extracted with 75 ml. of methylene chloride (three times). The combined organic layers are washed with an equal volume of water, dried over sodium sulfate, and evaporated to dryness to give the above titled oxazolidine. Purification is accomplished by column chromatography on silica gel, eluting with ethyl acetate/hexane (1:2, v/v).

Similarly, the phenols shown in Preparation 6 are converted to the respective oxazolidines.

EXAMPLE 8

This example illustrates further methods of converting the compounds of formula Ia into the corresponding compounds of formula Ib. In this example 1 mmole of 1-isopropylamino-3-(4-[2-(endobicyclo[3.1.0]hex-6-yl)ethylaminocarbonyl]phenoxy-2-propanol in 10 ml. of methanol is admixed with 20 ml. of 37% aqueous formaldehyde and then stirred at room temperature for one hour. The solvent is then removed by evaporation under vacuum affording a crude 5-(4-[2-(endobicyclo[3.1.0]-hex-6-yl)ethylaminocarbonyl]phenoxymethyl)oxazolidine residue which is then stirred in 50 ml. of ethyl ether and filtered. Gaseous hydrogen chloride is passed over the surface of the filtrate with rapid stirring until no further precipitate is formed. The precipitate is filtered off, washed with diethyl ether and then recrystallized from a mixture of propanol and diethyl ether affording 5-(4-[2-(endobicyclo-[2.1.0]hex-6-yl)ethylaminocarbonyl]phenoxymethyl)oxazolidine hydrochloride.

Similarly by following the same procedure, the products of Example 1 are respectively converted to the corresponding compounds of formula IB and their hydrochloride salts.

Obviously many modifications and variations of the invention, described herein above and below in the Claims, can be made without departing from the essence and scope thereof.

What is claimed is:

1. A compound of the formula

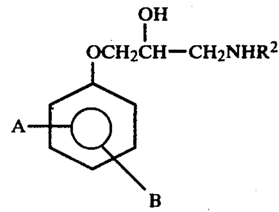

wherein $R^2$ is $C_1$ to $C_4$ linear or branched alkyl, $C_1$ to $C_4$ linear or branched carboalkoxy, nitrile or nitro; the group A is is hydrogen, halo, nitrile, $C_1$ to $C_2$ alkyl, $C_1$ to $C_2$ alkoxy, acetyl or propionyl; B is the group

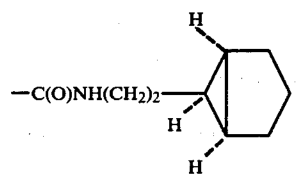

and pharmaceutically acceptable salts thereof with the proviso that when group B is at the 4 position of the carbocyclic aryl ring, the substituent A is at position 2 or 3 of said ring and when group B is at the 3 position of the carbocyclic aryl ring, the substituent A is at position 4 or 6 of said ring.

2. The compound of claim 1 wherein $R^2$ is selected from the group isopropyl and t-butyl.

3. The compound of claim 2 wherein $R^2$ is isopropyl, the group A is substituted at the 2 position of the carbocyclic aryl ring and the group B is substituted at the 4 position of said ring.

4. The compound of claim 3 wherein A is selected from the group hydrogen, halo, $C_1$ to $C_2$ alkyl, $C_1$ to $C_2$ alkoxy, nitrile, acetyl and propionyl.

5. The compound of claim 4 wherein A is hydrogen.

6. The compound of claim 4 wherein A is halo selected from the group fluoro, chloro, and bromo.

7. The compound of claim 6 wherein A is chloro.

8. The compound of claim 4 wherein A is nitrile.

9. The compound of claim 4 wherein A is acetyl or propionyl.

10. The compound of claim 2 wherein $R^2$ is t-butyl, the group A is substituted at the 2-position of the carbocyclic aryl ring and the group B is substituted at the 4 position of said ring.

11. The compound of claim 10 wherein A is selected from the group hydrogen, halo, $C_1$ to $C_2$ alkyl, $C_1$ to $C_2$ alkoxy, nitrile, acetyl and propionyl.

12. The compound of claim 11 wherein A is hydrogen.

13. The compound of claim 11 wherein A is halo selected from the group fluoro, chloro, and bromo.

14. The compound of claim 13 wherein A is chloro.

15. The compound of claim 11 wherein A is nitrile.

16. The compound of claim 11 wherein A is acetyl or propionyl.

17. The compound of claim 2 wherein $R^2$ is isopropyl, the group A substituted at the 3 position of the carbocyclic aryl ring and the group B is substituted at the 4 position of said ring.

18. The compound of claim 17 wherein A is selected from the group hydrogen, halo, $C_1$ to $C_2$ alkyl and $C_1$ to $C_2$ alkoxy.

19. The compound of claim 18 wherein A is hydrogen.

20. The compound of claim 18 wherein A is chloro.

21. The compound of claim 18 wherein A is selected from the group methoxy and ethoxy.

22. The compound of claim 18 wherein A is selected from the group methyl and ethyl.

23. The compound of claim 2 wherein $R^2$ is t-butyl, the group A substituted at the 3 position of the carbocyclic aryl ring and the group B is substituted at the 4 position of said ring.

24. The compound of claim 23 wherein A is selected from the group hydrogen, halo, $C_1$ to $C_2$ alkyl and $C_1$ to $C_2$ alkoxy.

25. The compound of claim 24 wherein A is hydrogen.

26. The compound of claim 24 wherein A is chloro.

27. The compound of claim 24 wherein A is selected from the group methoxy and ethoxy.

28. The compound of claim 24 wherein A is selected from the group methyl and ethyl.

29. The compound of claim 2 wherein $R^2$ is isopropyl, the group A is substituted at the 6 position of the carbocyclic ring and the group B is substituted at the 3 position of said ring.

30. The compound of claim 29 wherein A is selected from the group hydrogen, halo, $C_1$ to $C_2$ alkyl, $C_1$ to $C_2$ alkoxy, and nitrile.

31. The compound of claim 30 wherein A is hydrogen.

32. The compound of claim 30 wherein A is halo selected from the group chloro and bromo.

33. The compound of claim 32 wherein A is chloro.

34. The compound of claim 30 wherein A is cyano.

35. The compound of claim 30 wherein A is selected from the group methoxy and ethoxy.

36. The compound of claim 30 wherein A is selected from the group methyl and ethyl.

37. The compound of claim 2 wherein $R^2$ is t-butyl the group A is substituted at the 6 position of the carbocyclic aryl ring and the group B is substituted at the 3 position of said ring.

38. The compound of claim 37 wherein A is selected from the group hydrogen, halo, $C_1$ to $C_2$ alkyl, $C_1$ to $C_2$ alkoxy, and nitrile.

39. The compound of claim 38 wherein A is hydrogen.

40. The compound of claim 38 wherein A is halo selected from the group chloro and bromo.

41. The compound of claim 40 wherein A is chloro.

42. The compound of claim 38 wherein A is nitrile.

43. The compound of claim 38 wherein A is selected from the group methoxy and ethoxy.

44. The compound of claim 38 wherein A is selected from the group methyl and ethyl.

45. The compound of claim 2 wherein $R^2$ is isopropyl, the group A is substituted at the 4 position of the carbocyclic aryl ring and the group B is substituted at the 3 position of said ring.

46. The compound of claim 45 wherein A is selected from the group hydrogen, halo, $C_1$ to $C_2$ alkyl and $C_2$ to $C_2$ alkoxy.

47. The compound of claim 46 wherein A is chloro or bromo.

48. The compound of claim 46 wherein A is methyl or ethyl.

49. The compound of claim 46 wherein A is methoxy.

50. The compound of claim 2 wherein $R^2$ is t-butyl, the group A is substituted at the 4 position of the carbocyclic aryl ring and the group B is substituted at the 3 position of said ring.

51. The compound of claim 50 wherein A is selected from the group hydrogen, halo, $C_1$ to $C_2$ alkyl and $C_1$ to $C_2$ alkoxy.

52. The compound of claim 51 wherein A is chloro or bromo.

53. The compound of claim 51 wherein A is methyl or ethyl.

54. The compound of claim 51 wherein A is methoxy.

55. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 1 and mixtures thereof.

56. A pharmaceutical composition for treating hypertension disorders in mammals consisting essentially of a pharmaceutically acceptable carrier and an amount effective to treat hypertension of an agent selected from the group of compounds of claim 1 and mixtures thereof.

57. The compound of claim 1 wherein when said compound is a pharmaceutically acceptable salt said salt is selected from the group hydrochloride and maleate salt.

* * * * *